United States Patent

Fischer et al.

[11] Patent Number: 4,650,896
[45] Date of Patent: Mar. 17, 1987

[54] PREPARATION OF 2-ALKYL-4,4-DIACYLOXYBUT-2-ENALS

[75] Inventors: Rolf Fischer, Heidelberg; Joachim Paust, Neuhofen, both of Fed. Rep. of Germany

[73] Assignee: BASF Aktiengesellschaft, Ludwigshafen, Fed. Rep. of Germany

[21] Appl. No.: 730,686

[22] Filed: May 3, 1985

[30] Foreign Application Priority Data

May 19, 1984 [DE] Fed. Rep. of Germany ....... 3418747

[51] Int. Cl.[4] .................... C07C 67/29; C07C 69/025; C07C 69/145
[52] U.S. Cl. .................................. 560/112; 560/113; 560/121; 560/128; 560/231; 560/234; 560/261; 560/262; 260/410.9 N; 260/405.6; 568/484
[58] Field of Search ............... 560/262, 112, 113, 121, 560/128, 231, 234, 261; 568/484; 260/410.9 N

[56] References Cited

U.S. PATENT DOCUMENTS 4,410,719 10/1983 Fischer et al. ..................... 560/112

FOREIGN PATENT DOCUMENTS 68372 1/1983 European Pat. Off. .
89585 9/1983 European Pat. Off. .
3210705 10/1983 Fed. Rep. of Germany .

*Primary Examiner*—Paul J. Killos
*Attorney, Agent, or Firm*—John H. Shurtleff

[57] ABSTRACT

2-Alkyl-4,4-diacyloxybut-2-enals of the formula

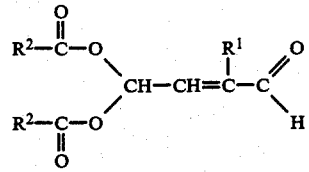

where $R^1$ is alkyl and $R^2$ is hydrogen or an aliphatic, cycloaliphatic or aromatic radical, are prepared by a process in which a 2-alkyl-1,4-diacyloxy-1,3-butadiene of the formula

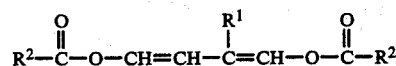

is reacted with oxygen or an oxygen donor in the presence of an acidic ion exchanger.

8 Claims, No Drawings

PREPARATION OF 2-ALKYL-4,4-DIACYLOXYBUT-2-ENALS

The present invention relates to a process for the preparation of 2-alkyl-4,4-diacyloxyloxybut-2-enals (2-alkylfumardialdehyde-4-monoacylals) by reacting a 2-alkyl-1,4-diacyloxy-1,3-butadiene with oxygen or an oxygen donor in the presence of an acidic ion exchanger.

2-Alkyl-4,4-diacyloxybut-2-enals can be prepared, for example, by reacting a 2-alkyl-1,4-diacyloxy-1,3-butadiene with oxygen or an oxygen donor in the presence of a carboxylic acid by the method described in European Pat. No. 68,372, or by heating a 2-alkyl-2,4-diacyloxybut-3-enal in a carboxylic acid by the method described in European Pat. No. 89,585. It has furthermore been disclosed that 2-alkyl-2,4-diacyloxybut-3-enals can be prepared by reacting a 2-alkyl-1,4-diacyloxy-1,3-butadiene with a percarboxylic acid in an inert solvent (European Pat. No. 89,586), and that 2-alkyl-4,4-diacyloxybut-2-enals are converted to 3-alkyl-2,5-dihydrofuran-2-ones on treatment with an acidic compound, such as a mineral acid, an acidic ion exchanger or a water-containing aliphatic carboxylic acid (German Laid-Open Application No. DOS 3,210,705).

Although the stated processes for the preparation of 2-alkyl-4,4-diacyloxybut-2-enals give reaction mixtures which contain the desired trans-2-alkyl-4,4-diacyloxybut-2-enal as the principal product, they have the disadvantage that the said reaction mixture may additionally contain significant amounts of 2-alkyl-2,4-diacyloxybut-3-enals and cis-2-alkyl-4,4-diacyloxybut-2-enals, so that the reaction mixture may have to be separated by a method which is expensive and entails large losses, eg. by fractional distillation. As Examples 1 and 2 of European Pat. No. 89,585 show, subsequent isomerization of 2-alkyl-2,4-diacyloxybut-3-enals to 2-alkyl-4,4-diacyloxybut-2-enals as a result of the formation of 3-alkyl-2,5-dihydrofuran-2-ones also leads to losses of the desired product.

It is an object of the present invention to provide a process for the preparation of 2-alkyl-4,4-diacyloxybut-2-enals which does not have the stated disadvantages and gives very high contents of trans-isomers, only trans-2-alkyl-4,4-diacyloxybut-2-enals being suitable as starting materials for terpene synthesis.

We have found that this object is achieved, and that 2-alkyl-4,4-diacyloxybut-2-enals of the formula

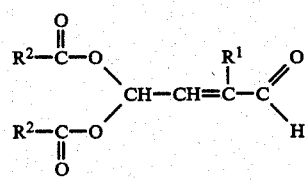

I where $R^1$ is alkyl of 1 to 5 carbon atoms and $R^2$ is hydrogen, an aliphatic radical of 1 to 15 carbon atoms, a cycloaliphatic radical of 5 to 7 carbon atoms or an aromatic radical, can particularly advantageously be prepared by reacting a 2-alkyl-1,4-diacyloxy-1,3-butadiene of the formula

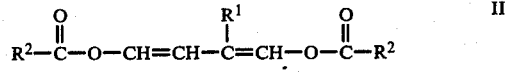

II where $R^1$ and $R^2$ have the above meanings, with oxygen or an oxygen donor, in a solvent, by a method in which the reaction is carried out in the presence of an acidic ion exchanger.

In the novel process, the 2-alkyl-4,4-diacyloxybut-2-enals are obtained from 2-alkyl-1,4-diacyloxy-1,3-butadienes with high selectivity and predominantly in the form of the trans-isomers.

In the case of the preparation of trans-2-methyl-4,4-diacetoxybut-2-enal from 2-methyl-1,4-diacetoxy-1,3-butadiene in glacial acetic acid as a solvent, the reaction can be illustrated by the following equation:

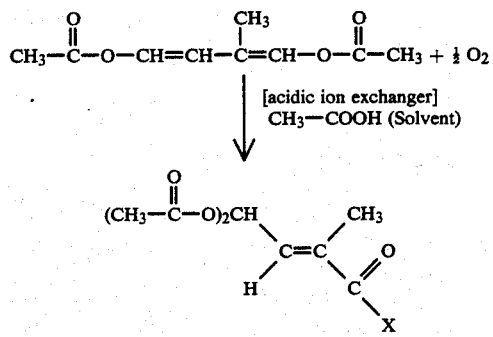

In the -alkyl-1-1,4 diacyloxy-1,3-butadienes of the formula II which are used as starting materials, $R^1$ is alkyl of 1 to 5, preferably 1 to 3, carbon atoms, and the two radicals $R^2$ can be identical or different and are each hydrogen, an aliphatic radical of 1 to 15 carbon atoms, a cycloaliphatic radical of 5 to 7 carbon atoms or an aromatic radical. Examples of aliphatic radicals are alkyl, such as methyl, ethyl, n-propyl, isopropyl, n-butyl, isobutyl, tert.-butyl, n-pentyl, palmityl or stearyl. Examples of suitable cycloaliphatic radicals are cyclopentyl, cyclohexyl and cycloheptyl. Aromatic radicals can be, for example, phenyl which is unsubstituted or substituted by alkyl or halogen.

Examples of compounds of the formula II are 2-methyl-, 2-ethyl-, 2-n-propyl-, 2-butyl- and 2-pentyl-1,4-diacetoxy-1,3-butadiene, 2-methyl-1-propionyloxy-4-acetoxy-1,3-butadiene, 2-methyl-1-acetoxy-4-palmityloxy-1,3-butadiene, 2-methyl-1-cyclohexyloxy-4-acetoxy-1,3-butadiene and 2-methyl-1-benzoyloxy-4-acetoxy-1,3-butadiene.

The starting compounds of the formula II can be prepared by, for example, acetylation of 2-alkyl-4-acyloxybut-2-enals with acetic anhydride (J.Org.Chem. 41 (1976), 2625) or pyrolysis of 2-alkyl-3,4-diacetoxytricyclo[4,2,1,02,5]non-7-enes (J.Chem.Soc., Chem. Comm. 1974, pages 956 to 957).

Oxygen can be used in pure form or as a mixture with other gases, such as nitrogen, eg. in the form of air, or with other inert gases, such as carbon dioxide. Examples of suitable oxygen donors are those which are used for the epoxidation of olefins, eg. hydrogen peroxide, anthraquinone peroxides, peracids, such as performic acid, peracetic acid, perpropionic acid, perbenzoic acid, m-chloroperbenzoic acid, per-n-butyric acid or per-isobutyric acid, and organic hydroperoxides, such as tert.-butyl hydroperoxide or cumene hydroperoxide.

Compounds of this type are stated in, for example, Ullmanns Encyclopädie der Technischen Chemie, 4th Edition, Volume 10, pages 563–567. The oxygen and the oxygen donor can also be used in the presence of an epoxidation catalyst.

The acidic ion exchangers used are cation exchangers in their acidic form, for example exchangers composed of styrene and divinylbenzene and containing sulfo groups, inorganic cation exchangers, such as zeolites, phenol- or polystyrenesulfonic acid resins, styrenephosphonic acid resins or styrenephosphinic acid resins, and corresponding exchangers containing acidic resins, eg. bi-functional condensation resins. Examples of cation exchangers of the stated type are the products available commercially under the names ®Lewatit S 100, ®Amberlite IR-120, ®Lewasorb, ®Dowex 50 WX 8 and ®Amberlyst 15. Strongly acidic ion exchangers are particularly preferred for this purpose.

The amount of cation exchanger depends on the selectivity or the number of exchangeable groups in the exchanger used at the reaction temperature. In general, from 0.5 to 40, preferably from 3 to 25, % by weight, based on the starting materials II, of exchanger are employed.

It is in principle also possible for the reaction mixtures obtained in the reaction of the 2-alkyl-1,4-diacyloxy-1,3-butadiene with oxygen or the oxygen donor to be heated subsequently together with an ion exchanger. However, the yields of 2-alkyl-4,4-diacyloxybut-2-enals obtainable in this manner, and the content of trans-2-alkyl-4,4-diacyloxybut-2-enals, are somewhat lower than in the case of the simultaneous reaction.

Examples of suitable solvents are carboxylic acids, such as formic acid, acetic acid, propionic acid, butyric acid, valeric acids, caproic acids, lauric acid, oleic acid, palmitic acid, cyclohexanecarboxylic acid, benzoic acid and phenylacetic acid. For economic reasons, acetic acid is particularly preferred. The carboxylic acid is generally used in excess, for example in an amount of from 1 to 80 moles per mole of the 1,3-diene II employed. In general, the carboxylic acid from which the acyloxy groups are derived is used. Instead of carboxylic acids, it is also possible to use other solvents which are inert under the reaction conditions. Examples of suitable solvents of this type are carboxylates, such as methyl acetate, chlorohydrocarbons, such as methylene chloride, chloroform, carbon tetrachloride or 1,2-dichloroethane, hydrocarbons, such as alkanes, benzene and alkylbenzenes, and ethers, such as diethyl ether, tetrahydrofuran or dioxane. Advantageously, from 0.1 to 80, in particular from 2 to 60, moles of the solvent which is inert under the reaction conditions are employed per mole of starting compound II.

The novel process is carried out, for example, as follows: from 0.5 to 10, in particular from 1 to 3, moles of oxygen or of an oxygen donor are used per mole of starting compound II, the reaction advantageously being carried out at from 0° to 200° C., in particular from 20° to 120° C. The oxygen pressure used is, for example, from 1 to 100, in particular from 1 to 20, bar.

The process can be carried out batchwise or continuously, under atmospheric or superatmospheric pressure. Unconverted 1,3-dienes II can, if necessary, be removed from the resulting 2-alkyl-4,4-diacyloxybut-2-enals by distillation after the reaction, and can be reused for the reaction according to the invention.

The novel reaction can be carried out, for example, as follows: the ion exchanger is suspended in a solution of the starting compound II in the particular solvent, and is reacted with oxygen or an oxygen donor at the particular reaction temperature. When the reaction is complete, the ion exchanger is filtered off or removed by centrifuging, and the reaction mixture is worked up by, for example, distillation. However, it is also possible to pass a solution of the starting compound II over a fixed-bed ion exchanger, and to work up the reaction mixture subsequently.

The trans-2-alkyl-4,4-diacyloxybut-2-enals obtainable with high selectivity by the novel process are useful intermediates for the preparation of terpenes such as retinal, $\beta$-carotene (German Laid-Open Application DOS 2,357,810) and apocarotinoids.

EXAMPLE 1

10 g of the acidic ion exchanger obtainable commercially under the name ®Amberlite IR-120 (H form) were suspended in a solution of 184 g of 2-methyl-1,4-diacetoxy-1,3-butadiene, 357 g of acetic anhydride and 1,000 g of glacial acetic acid. Before being used, the ion exchanger was washed water-free with glacial acetic acid. 81.6 g of 50% strength hydrogen peroxide were added to the stirred reaction mixture at 100°±2° C. in the course of 55 minutes, after which stirring was continued for a further 35 minutes at this temperature. After this period, per compounds were no longer detectable by iodometric titration. The mixture was cooled and the ion exchanger was then filtered off. Acetic acid and acetic anhydride were distilled off in a rotary evaporator at 70° C. and under 25 mbar, and low boilers were distilled off in a Sambay apparatus at 90° C. and under 5 mbar. The reaction mixture was subjected to a Sambay distillation at 150° C. and under 0.7 mbar, 110 g (55%, based on 2-methyl-1,4-diacetoxy-1,3-butadiene employed) of-2-methyldiacetoxybutenals being obtained.

In the $^1$H-NMR spectrum (CDCl$^{13}$ as solvent), the signals for the aldehyde protons of the various 2-methyldiacetoxybutenals showed that the ratio of trans- to cis-2-methyl-4,4-diacetoxybut-2-enal was 92:8. Starting material and 2-methyl-2,4-diacetoxybut-3-enals were not present.

COMPARATIVE EXAMPLE 1

The procedure described in Example 1 was followed, except that the reaction was carried out in the absence of the ion exchanger. The yield of methyldiacetoxybutenals was 59%, based on 2-methyl-1,4-diacetoxy-1,3-butadiene employed. The ratio of trans- (aldehyde proton: 9.45 ppm) to cis-2-methyl-4,4-diacetoxybut-2-enal (aldehyde proton: 10.25 ppm) was 74:26. The 2-methyldiacetoxybutenal mixture also contained 7% of trans- (aldehyde proton: 9.28 ppm) and 10% of cis-2-methyl-2,4-diacetoxybut-3-enal (aldehyde proton: 9.37 ppm), the percentages being based on the 2-methyldiacetoxybutenals. Starting material was not present.

EXAMPLE 2

200 cm$^3$/hour of a glacial acetic acid solution containing 10% by weight of 2-methyl-1,4-diacetoxy-1,3-butadiene and 32 l/hour of air were fed, at an internal temperature of 85°±2° to C. and under a total pressure of 2 bar, into a ®Hastelloy autoclave which had a paddle stirrer (1,000 rpm) and a free volume of 0.3 l and contained 100 g of ®Amberlite IR 120 (H form) in a vessel which had sieve-like walls and through which the reaction solution flowed. After a reaction time of 132 hours under the stated conditions, the reacted mixture obtained in the subsequent 12 hours (2,440 g) was collected and worked up. To do this, acetic acid and low boilers were separated at 60° C. and under 20 mbar in a rotary evaporator, and at 90° C. and under 7 mbar in a Sambay evaporator. The residue which remained was subjected to two successive distillation procedures in a Sambay apparatus at 150° C. and under 1 mbar to give 130 g (50%, based on 2-methyl-1,4-diacetoxy- 1,3-butadiene employed) of 2-methyldiacetoxybutenals.

In the $^1$H-NMR spectrum (CDCl$_1$ as solvent), the signals for the aldehyde protons of the various 2-methyldiacetoxybutenals showed that the ratio of trans- to cis-2-methyl-4,4-diacetoxybut-2-enal was 88:12. Starting material and 2-methyl-2,4-diacetoxybut-3-enals were not present.

COMPARATIVE EXAMPLE 2

The procedure described in Example 2 was followed, except that the reaction was carried out in the absence of the ion exchanger. The yield of methyldiacetoxybutenals was 50%, based on 2-methyl-1,4-diacetoxy-1,3-butadiene employed. The ratio of trans- (aldehyde proton: 9.45 ppm) to cis-2-methyl-4,4-diacetoxybut-2-enal (aldehyde proton: 10.25 ppm) was 82:18. The 2-methyldiacetoxybutenal mixture also contained 18% of trans- (aldehyde proton: 9.28 ppm) and 17% of cis-2-methyl-2,4-diacetoxybut-3-enal (aldehyde proton: 9.37 ppm), the percentages being based on 2-methyldiacetoxybutenals. Starting material was not present.

We claim:

1. A process for the preparation of a 2-alkyl-4,4-diacyloxybut-2-enal of the formula

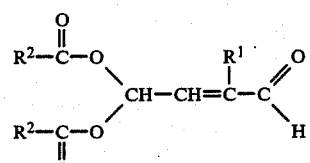

where $R^1$ is alkyl of 1 to 5 carbon atoms and $R^2$ is hydrogen, an aliphatic radical of 1 to 15 carbon atoms, a cycloaliphatic radical of 5 to 7 carbon atoms or an aromatic radical, wherein a 2-alkyl-1,4-diacyloxy-1,3-butadiene of the formula

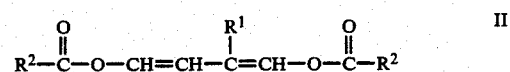

where $R^1$ and $R^2$ have the above meanings, in a carboxylic acid solvent, is treated with oxygen or an oxygen donor at from 0° to 200° C. and in the presence of an acidic ion exchanger.

2. A process as claimed in claim 1, wherein from 0.5 to 10 moles of oxygen or an oxygen donor are used per mole of starting compound of the formula II.

3. A process as claimed in claim 1, wherein the oxygen donor used is nydrogen peroxide, an anthraquinone peroxide, a per acid or an organic hydroperoxide.

4. A process as claimed in claim 1, wherein the acidic ion exchanger used is a cation exchanger in its acid form.

5. A process as claimed in claim 1, wherein the ion exchanger is used in an amount of from 0.5 to 40% by weight, based on the starting material II.

6. A process as claimed in claim 1, wherein the carboxylic acid is selected from the group consisting of formic acid, acetic acid, propionic acid, butyric acid, valeric acids, caproic acids, lauric acid, oleic acid, palmitic acid, cyclohexanecarboxylic acid, benzoic acid and phenylacetic acid.

7. A process as claimed in claim 1, wherein the carboxylic acid is acetic acid.

8. A process as claimed in claim 1, wherein the carboxylic acid is used in an amount of from 1 to 80 moles per mole of the butadiene II.

* * * * *

UNITED STATES PATENT AND TRADEMARK OFFICE
CERTIFICATE OF CORRECTION

PATENT NO.  : 4,650,896
DATED       : March 17, 1987
INVENTOR(S) : Rolf Fischer and Joachim Paust It is certified that error appears in the above-identified patent and that said Letters Patent is hereby corrected as shown below:

Claim 3, line 2:  change "nydrogen" to --hydrogen--.

Signed and Sealed this

Eighteenth Day of August, 1987

*Attest:*

DONALD J. QUIGG

*Attesting Officer*  *Commissioner of Patents and Trademarks*